(12) United States Patent
Schäfer et al.

(10) Patent No.: US 10,057,997 B2
(45) Date of Patent: Aug. 21, 2018

(54) DEVICE FOR INTEGRATING A SCREEN OR MONITOR IN A CASE

(71) Applicant: B. BRAUN AVITUM AG, Melsungen (DE)

(72) Inventors: Oliver Schäfer, Neuenstein (DE); Christian Schleicher, Dipperz (DE)

(73) Assignee: B. BRAUN AVITUM AG, Melsungen (DE)

( * ) Notice: Subject to any disclaimer, the term of this patent is extended or adjusted under 35 U.S.C. 154(b) by 0 days.

(21) Appl. No.: 15/497,895

(22) Filed: Apr. 26, 2017

(65) Prior Publication Data

US 2017/0325340 A1 Nov. 9, 2017

(30) Foreign Application Priority Data

May 3, 2016 (DE) .......................... 10 2016 108 201

(51) Int. Cl.
*H05K 5/00* (2006.01)
*A61M 1/14* (2006.01)
(Continued)

(52) U.S. Cl.
CPC ............. *H05K 5/0017* (2013.01); *A61M 1/14* (2013.01); *G02F 1/133308* (2013.01);
(Continued)

(58) Field of Classification Search
CPC ............... A61M 1/14; A61M 2205/502; G02F 1/133308; G02F 2001/133322;
(Continued)

(56) References Cited

U.S. PATENT DOCUMENTS 6,353,465 B1 3/2002 Hashimoto et al.
7,423,878 B2 * 9/2008 Kim .................... H05K 7/20963
345/905
(Continued)

FOREIGN PATENT DOCUMENTS

DE 11 01 564 3/1961
DE 101 20 594 11/2001
(Continued)

OTHER PUBLICATIONS

German Search Report (translation) for DE 10 2016 108 201.5 dated Mar. 1, 2017.
European Search Report for European Application No. 17 168 529.0, dated Sep. 26, 2017 with translation, 12 Pages.

*Primary Examiner* — James Wu
(74) *Attorney, Agent, or Firm* — RatnerPrestia

(57) ABSTRACT

A device for integrating a monitor in a case comprises a support element made from plastic material and having a recess which corresponds to a predetermined visible area of the monitor. The support element includes a plurality of apertures which are arranged at a predetermined distribution outside the recess for passing through positioning and/or retaining elements and placing the support element at a predetermined position on a sheet-metal case in which the support element can be received, and a frame section which projects from a base area of the support element on a rear side thereof and is arranged in sandwich design for receiving components of the monitor. The components of the monitor received in the frame section are adapted to be fixed to the support element, and the support element is adapted to be fixed to the at least one of positioning or retaining elements on the sheet-metal case.

13 Claims, 2 Drawing Sheets

(51) Int. Cl.
   *G06F 1/16* (2006.01)
   *G06F 3/041* (2006.01)
   *H05K 5/04* (2006.01)
   *H05K 7/14* (2006.01)
   *G02F 1/1333* (2006.01)

(52) U.S. Cl.
   CPC .......... *G06F 1/1637* (2013.01); *G06F 3/0412* (2013.01); *H05K 5/04* (2013.01); *H05K 7/1401* (2013.01); *A61M 2205/502* (2013.01); *G02F 2001/133322* (2013.01); *G02F 2201/46* (2013.01)

(58) Field of Classification Search
   CPC .. G02F 2201/46; G06F 1/1637; G06F 3/0412; H05K 5/0017; H05K 5/04; H05K 7/1401
   See application file for complete search history.

(56) References Cited

U.S. PATENT DOCUMENTS

| | | |
|---|---|---|
| 2001/0035442 A1 | 11/2001 | Yokobori |
| 2002/0061736 A1 | 5/2002 | Boman et al. |
| 2005/0067956 A1 | 3/2005 | Kim |
| 2005/0213924 A1 | 9/2005 | Sakurai et al. |
| 2008/0200868 A1* | 8/2008 | Alberti .................. A61M 1/28 604/29 |

FOREIGN PATENT DOCUMENTS

| | | |
|---|---|---|
| DE | 202 18 586 | 2/2003 |
| JP | 06237086 A | 8/1994 |
| WO | 2008157200 A1 | 12/2008 |

\* cited by examiner

DEVICE FOR INTEGRATING A SCREEN OR MONITOR IN A CASE

CROSS REFERENCE TO RELATED APPLICATIONS

This application claims priority to German application DE 10 2016 108 201.5 filed May 3, 2016, the contents of such application being incorporated by reference herein.

FIELD OF THE INVENTION

The invention relates to a device for integrating a screen or monitor in a case and especially relates to a device for monitor integration with plastic frames in a sheet-metal case, especially in a sheet-metal case of a medical device or a dialysis machine.

BACKGROUND OF THE INVENTION

In machines for extracorporeal blood treatment monitor assemblies are known which are either integrated in statically defined load-bearing metal cases, which at the same time constitute a visible case surface, or are integrated in statically defined metal frames, which receive monitor components and include a plastic cover as a case-forming surface.

Although monitor cases, which are, for example, manufactured from cast metal, ensure required mechanical properties, properties relating to EMC (electromagnetic compatibility) and functional integration, these cases are very expensive due to the high manufacturing expenditure with appropriate refinement, where necessary. It is another drawback of these solutions that in a load-bearing metal case the outer case-forming design is formed to be integrated and in this way multiple use is not possible by reason of different design features and thus differences from other monitor assemblies.

In systems making use of a plastic case, the plastic case manufactured with injection molding, for example, usually is not adapted by itself to ensure mechanical properties, for example required evenness and/or torsional stiffness in the case of a touch-sensitive screen, which properties are necessary, however, to guarantee failure-free functioning. Therefore, such plastic cases usually only constitute a decorative cover whereas inside a metallic frame for receiving the monitor components is employed. Another drawback in case-forming components of plastic material consists in a low electromagnetic immunity. Sufficient immunity can only be achieved in this case with specific and additional coating on the plastic part.

SUMMARY OF THE INVENTION

Therefore, it is an object underlying the invention to overcome the afore-mentioned drawbacks and to provide an improved device for integrating a screen or monitor in a case.

In particular, such device is to be provided especially for a dialysis machine as an example of a machine for extracorporeal blood treatment.

This object is achieved, according to aspects of the invention, by a device for integrating a monitor in a case comprising the features of the independent claim and by a dialysis machine as defined in the claims. Advantageous developments of the invention are the subject matter of the enclosed subclaims.

The general idea underlying the invention is to receive all components which are relevant to transfer of information and interaction, such as a touch-sensitive part, a flat screen (TFT), a status display, operating elements (physically configured keys and switches), printed circuit boards and the like, in a multi-functional plastic frame and to integrate them in a sheet-metal case which may be separately provided or may at the same time constitute a machine case.

Material properties and a geometry of the multi-functional plastic frame ensure, together with the material properties of the sheet-metal case and further stiffening elements arranged in a stacked array or sandwich design, sufficient stiffness for the functioning of the touch-sensitive components (touch panel). This helps to increase the functionality of the case. Apart from decorative elements becoming evident on visible parts, the case moreover develops a primary effect for an overall functionality of the touch panel and TFT integration. The sandwich design comprising a plastic frame can be manufactured at lower cost than the known solutions in the case of machines for extracorporeal blood treatment.

The integration in a metal case made from sheet steel eliminates influences by electromagnetic interferences, as compared to monitor cases made from plastic, and thus eliminates the additional EMC coating required in a plastic case. Moreover, when standardized interfaces are utilized, the option of integration in different sheet-metal cases is given, for example in a separate monitor sheet-metal case which is e.g. attached to be rotatable on a machine case, or in a body-type machine case made from sheet metal. In this way, said frame and the complete assembly may be installed in most various apparatuses as carry over parts. Simultaneously, the plastic frame partly visible on the front end e.g. in a recess of the sheet-metal case constitutes a transition to the painted sheet-metal case which can be visually emphasized.

In detail, the afore-listed advantages are realized and the object is achieved by a device for integrating a monitor in a case comprising a support element made from plastic material and including a recess which corresponds to a predetermined visible area of the monitor, wherein the support element includes a plurality of apertures which are arranged at a predetermined distribution outside the recess for passing through positioning and/or retaining elements and placing the support element at a predetermined position on a sheet-metal case in which the support element can be received, and a frame section projecting from a base area of the support element on a rear side thereof and being arranged for receiving components of the monitor in sandwich design, wherein the components of the monitor received in the frame section can be fixed to the support element and the support element can be fixed to the positioning and/or retaining elements on the sheet-metal case.

Preferably, at least one of the components of the monitor is configured to have a defined inherent rigidity for backing the components of the monitor received in the frame section fully on the rear side and includes at least one circumferentially arranged fixing section which is arranged for fixing the at least one component of the monitor to the support element.

Preferably, the at least one component of the monitor is arranged to provide electric connectivity for at least one electronic subassembly with respect to the components of the monitor and/or to fix the electronic subassembly.

Preferably, the device is provided with at least one stiffening element which is arranged to fix the support element including the components of the monitor received in the frame section to the sheet-metal case.

Preferably, the at least one stiffening element is arranged to fix an electronic subassembly with respect to the components of the monitor.

Preferably, the at least one stiffening element is made from a metal and may be fixed by screwing.

Preferably, the at least one component of the monitor can be screw-connected to the support element made from plastic. Accordingly, the component of the monitor may advantageously be an imaging element such as a liquid crystal display means or TFT display means and may be adapted to be screw-connected to the support element in plastic material with securing structures integrally formed with the imaging element.

Preferably, the at least one stiffening element is adapted to be screw-connected to at least a part of the positioning and/or retaining elements of the sheet-metal case which are made from metal.

Preferably, the support element includes, projecting from the rear side, at least a first retaining means arranged along a periphery of the support element for screw-connecting at least one attaching part, e.g. the case rear wall and/or the support element, to the sheet-metal case and/or includes at least a second retaining means arranged along a periphery of the frame section for screw-connecting the at least one component of the monitor.

Preferably, the recess of the support element has a smaller periphery than a recess of the sheet-metal case so that a predetermined section of the support element, which frames the recess of the sheet-metal case on the inside, is visible on the front end of the sheet-metal case.

Preferably, the components of the monitor include at least one touch-sensitive transparent and flat element which is arranged to provide a sealing effect and/or to compensate for tolerances, and an imaging element which are arranged to be stacked in the frame section of the support element and form a touch-sensitive screen.

Preferably, the support element, a sealing element arranged between the support element and one of the components of the monitor as well as the components of the monitor are arranged for being pre-assembled and being mounted as a functionally ready-to-connect subassembly into the sheet-metal case and being connected thereto.

Preferably, the device comprises a sub-frame adapted to be inserted in the frame of the support element and being arranged to reduce the size of the frame and/or of the recess of the support element.

Especially advantageously, a dialysis machine may be arranged to comprise a device for integrating a monitor as afore-described, wherein the sheet-metal case is a case or a body of a dialysis machine.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
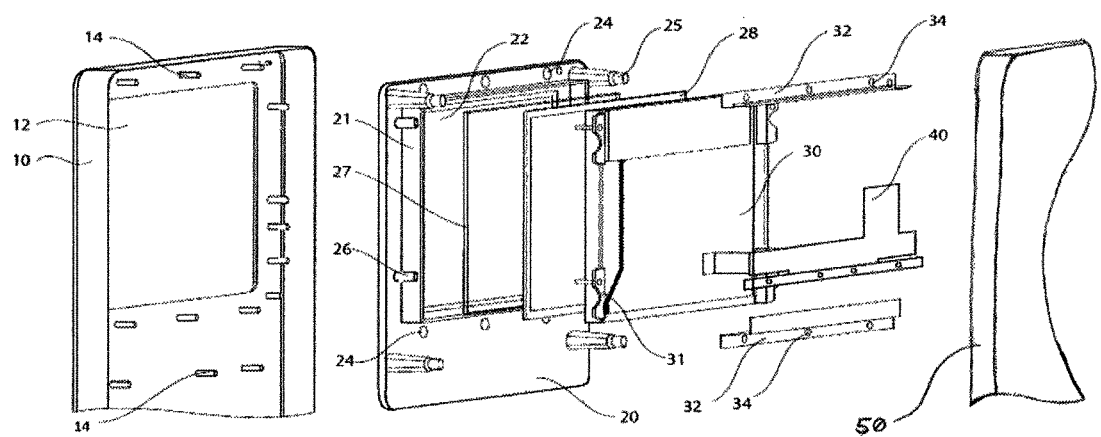
FIG. 1 shows a device for integrating a monitor in a sheet-metal case according to the embodiment in a simplified exploded view.
Figure 2:
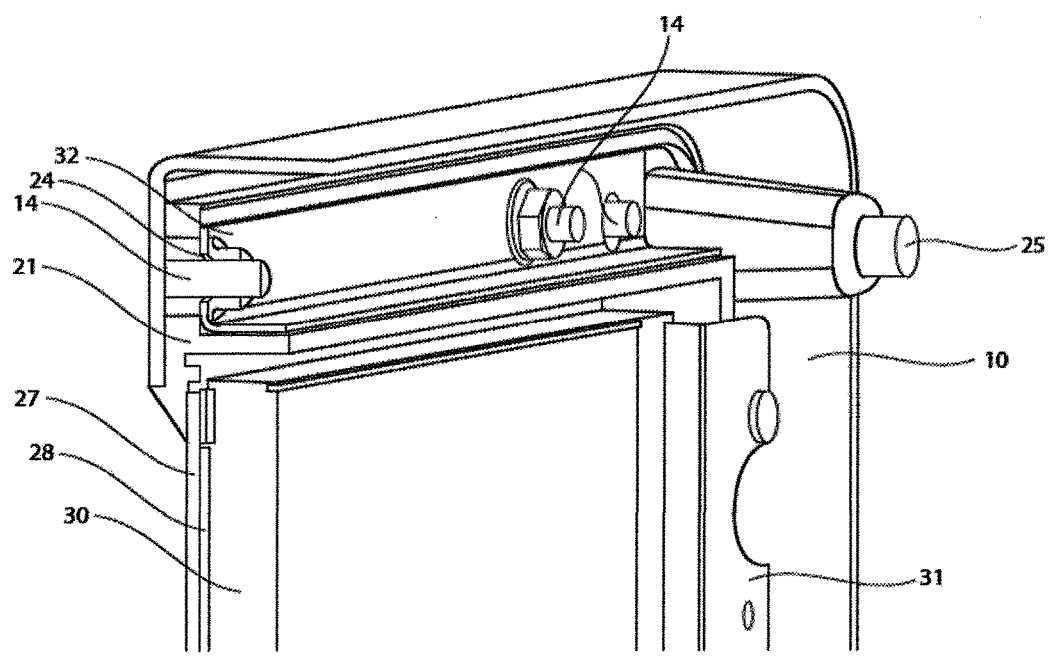
FIG. 2 shows a schematic cutout view of the device for integrating a monitor in a condition of being mounted in the sheet-metal case as shown in FIG. 1.

In the following description of figures equal or equally acting elements and/or components will be denoted equally and/or with the same reference numerals and reasonably will not be redundantly described. In cases in which a subsequent embodiment functionally corresponds to at least a preceding one, i.e. corresponding functions, arrangements and/or process or operating cycles are equally comprised, reasonably only differences will be discussed.

As is shown in FIG. 1, a sheet-metal case 10, which may be, for example, a case or a body of a medical apparatus or a dialysis machine, has a recess 12 forming a type of window and being arranged to permit the view to a screen of a monitor which can be installed into the case or can be attached to the case. On a rear side of the sheet-metal case 10 facing the interior of the apparatus, preferably plural, for example pin-shaped, elevations 14 are dispersed arranged which serve as positioning and/or retaining elements and, in combination with corresponding apertures of an attaching part to be mounted, enable the attaching part to be positioned with respect to the housing wall (i.e. wall of the case) at a predetermined position. For configuring a retaining element, the pin-shaped elevations 14 preferably comprise a threaded arrangement (female thread (in the case of hollow pin shape) and/or male thread) to which the attaching part can be fixed with a screwed connection, for example.

According to the embodiment, an attaching part of the afore-mentioned type forms especially a support element 20 which constitutes a frame made from plastic and as such sort of a base plate having a base area. The support element 20 equally includes a recess 22 corresponding to the recess 12 of the sheet-metal case and corresponding to a predetermined visible area of the monitor. Moreover, outside the recess 22 the support element 20 includes a plurality of piercing apertures 24 the position and/or distribution of which on the support element 20 correspond(s) to the positions of the elevations 14 on the sheet-metal case 10 so that the elevations 14, as positioning and/or retaining elements as well as for placing the support element 20 at a predetermined position on the sheet-metal case 10 in which the support element 20 can be received, can be passed through the apertures 24.

In a manner surrounding or framing the recess 22 of the support element 20, on the support element 20 furthermore a frame section or frame 21 is formed which projects from the base area of the support element 20 on the rear side thereof and serves for receiving a sealing element 27 as well as components 28 and 30 of a monitor and, respectively, a screen in sandwich design. The dimensions (height, width, depth) of the frame 21 are selected so that, while functionally interacting, the monitor components 28 and 30 can be inserted in the frame 21, can be electrically connected and can be retained or fixed on the support element 20 in a stationary manner. The support element 20 itself can be fixed to the sheet-metal case 10 with the elevations 14. The frame 21 equally consisting of plastic material advantageously contributes, as part of a three-dimensional shape, to the torsional resistance of the support element 20 without significantly increasing the total weight thereof.

The sealing element 27 is disposed between the monitor component 28 and the support element 20. It is intended to protect the monitor component 28 against damage by the support element 20 and to prevent moisture and dirt from penetrating.

The projecting frame 21 serves as stiffening of the support element 20 and guides the sealing element 27 and the monitor components 28 and 30 by an appropriate geometry. The sealing element 27 as well as the monitor component 28 are clamped and thereby fixed in their position via the monitor component 30 which is screwed to the support element 20 with securing elements 31 that may as well be configured as receiving and stiffening elements.

According to the embodiment, the monitor component 30 has a particular inherent rigidity and, as so-to-speak the last sandwich component, can be placed onto the components 27 and 28 received in the frame 21 before, i.e. the sealing element 27 and e.g. a touch-sensitive transparent and flat touch film 28, so that it maintains and supports them in the placed state flatly on the rear side. On the periphery of the monitor component 30 a predetermined number of securing elements 31 is arranged for securing or retaining on the support element 20. The securing elements 31 may be tab-shaped and/or angled, for example, having a through opening through which a securing element 31, such as a screw, can be guided and can be fixed to the support element 20 in an elevation 26 which is preferably also round or pin-shaped. In this embodiment, at each corner area of the monitor component 30 a securing element 31 is used, consequently a total of four securing elements 31. However, the number and/or a material of the securing elements 31 is/are not further restricted as long as the monitor components 28 and 30 are ensured to be retained and supported in a failsafe and functionally compatible manner. For example, also a diagonal structure joining two corner areas on the rear side of the monitor component 30 or a cross structure joining four corner areas or central areas can be realized.

The monitor component 30 may include or provide in a manner adapted for coupling mechanical and/or electrical terminals or connecting elements which provide for at least one electronic subassembly and, respectively, one carrier element for electric components 40 electric connectivity with respect to the monitor components 28 and 30 of the monitor. In this way, optionally required control electronics, processing electronics, a power supply, an interface and/or the like may advantageously become part of the entire assembly 40 which then can be connected to the rear side of the monitor component 30.

In accordance with the embodiment, a holder 32 forming a stiffening element is provided. The holder 32 preferably is made from metal which may be configured e.g. as an angle plate and is arranged to fix the support element 20 with the components 28 and 30 of the monitor received in the frame section 21 to the sheet-metal case 10. For this purpose, the holder 32 in this embodiment includes a number of apertures 34 corresponding as to size and position to a relevant part or a relevant number of the elevations 14 and the apertures 24 on the support element 20 so that at first the support element 20 (optionally partly or completely pre-assembled to form the monitor assembly) can be loosely placed by the sheet-metal case 10 by passing the elevations 14 through the apertures 24, then the holder 32 can be loosely placed by the support element 32 by passing the elevations 14 also through the apertures 34, and finally a screwed connection at the threaded arrangement of the elevations 34 fixes the holder 32 including the support element 20 located there beneath to or, respectively, against the sheet-metal case 10, e.g. with a screw joint. In other words, the holder 32 as the at least one stiffening element can be screwed to at least part of the elevations 14 made from metal as the positioning and/or retaining elements of the sheet-metal case 10. The holder 32 in this frame may likewise be designed to link and retain the electronic subassembly 40 simultaneously and, respectively, through the same screw joints. The electronic subassembly 40 may alternatively be mounted and fastened on the metal sheet case 10.

For attaching parts, such as e.g. the rear case wall 50, furthermore an alternative securing, backing and/or retaining device may be provided. The support element 20 may include, for this purpose, on the rear side and projecting from the base plate or base area at least a first retaining means 25 which is arranged along the periphery of the support element 20, for example in the respective corner areas thereof, and is designed so that an attaching part can be fastened thereto and/or the support element 20 can be fastened to the sheet-metal case 10.

In an embodiment of the device according to the embodiment, the recess 22 of the support element 20 has a smaller periphery than a recess 12 of the sheet-metal case 10 so that on the front end of the sheet-metal case 10, i.e. for a user standing in front of the case, a predetermined section of the support element 20 is visible in the recess 12 of the sheet-metal case 10.

It is noted that the components 28 and 30 of the monitor comprise at least one touch-sensitive transparent and flat element 28 (touch film) and an imaging element 30 (liquid-crystal display, TFT) which are arranged to be stacked in the frame section 21 of the support element 20 and form a touch-sensitive screen 28, 30. For this purpose, a screen or display module prefabricated in so far may be used. The support element 20, the sealing element 27 as well as the components 28 and 30 of the monitor are preferably pre-assembled as system-, apparatus- and/or model-independent carry over parts and are inserted in the metal sheet case 10 as a functionally ready-to-connect subassembly, for example a housing or body of a dialysis machine, and are connected thereto.

As afore-described, a monitor integration in sandwich design with an inner plastic frame in a sheet metal for machines comprising a machine case made from sheet metal advantageously facilitates direct monitor integration in an existing sheet-metal case. The increased functional integration of the components allows for efficient monitor integration. Moreover, a shared component strategy is enabled by standardization.

In a modification of the afore-described embodiment, a reducing sub-frame (insert frame, insert or reducing adapter) (not shown) may be provided for adapting the original size of the frame 21 and/or the recess 22 by reducing to dimensions of monitor components provided by specific development or economically available on the market at a particular time. Such sub-frame may be adapted to be inserted in the (main) frame 21 and to be supported on, i.e. to rest on and/or snap in or engage in, supporting points or supporting faces arranged there and/or to be provided with an appropriately fitting lining on the front end and/or the rear end, and to be configured in total so that the originally present securing means of the support element 20 continue to be usable. For this purpose, the sub-frame may advantageously be adapted to be inserted from the front side of the support element 20 into the recess 22, wherein the cover of the sub-frame extends into the surface of the sheet-metal case 10 and covers also the frame section of the support element 20 possibly visible in the recess 12 of the sheet-metal case, and wherein an engaging device of the sub-frame engages behind the frame 21 of the support element 20 and latches the sub-frame in the frame 21. In this way, on a constant basis formed by the support element 20, the monitor component 30 adapted thereto as well as the holder 32, depending on e.g. the availability of monitor components or development specifications, monitor components having a different, e.g. smaller, screen diagonal or a different image side ratio can be installed, where needed. Thus, in turn, within one model series cheaper basic models having a less specified monitor can be provided and/or such cheaper basic models are later expandable in the case of increased demands and it is possible, within the scope of spare parts supply, to provide suitable monitor components in the long run.

It is understood that the invention is not limited to the described embodiment and the modifications thereof, but that within the scope of protection defined by the following claims combinations of at least parts of said embodiments, modifications and equivalents may be equally obvious to those skilled in the art.

The invention claimed is:

1. A device for integrating a monitor in a sheet-metal case, the device comprising:
   a sheet-metal case having a plurality of positioning elements extending from a rear side of the sheet-metal case;
   a support element made from plastic material and having a recess corresponding to a predetermined visible area of the monitor, the support element comprising:
      a plurality of apertures arranged in a predetermined distribution outside the recess through which the plurality of positioning elements of the sheet-metal case pass to fix the support element to the sheet-metal case, wherein the support element is received within the sheet-metal case such that the support element is placed at a predetermined position on the sheet-metal case;
      a frame section projecting from a base area of the support element on a side of the support element facing away from the positioning elements of the sheet-metal case; and
      a plurality of elevations extending from the side of the support element facing away from the positioning elements of the sheet-metal case, the plurality of elevations arranged along a periphery of the frame section;
   components of the monitor, wherein the frame section is configured to receive the components of the monitor, and at least one component of the monitor has a securing element configured to engage with at least one of the plurality of elevations of the support element such that the components of the monitor are fixed to the support element;
   wherein the support element is arranged between the components of the monitor and the sheet-metal case.

2. The device according to claim 1, wherein at least one of the components of the monitor has a defined inherent rigidity for backing the components of the monitor received in the frame section fully on the side of the support element facing away from the positioning elements of the sheet-metal case, and wherein the at least one of the components of the monitor includes at least one peripherally arranged fixing section to fix at least one of the components of the monitor on the support element.

3. The device according to claim 1, wherein the at least one component of the monitor is arranged to provide electric connectivity for at least one electronic sub-assembly with respect to the components of the monitor.

4. The device according to claim 1, further comprising:
   at least one holder having one or more apertures corresponding to the plurality of apertures of the support element and the plurality of positioning elements of the sheet-metal case, wherein the plurality of positioning elements of the sheet-metal case are passed through the apertures of the support element and the apertures of the holder, wherein the holder is fixed to the support element with at least one screw.

5. The device according to claim 4, wherein the at least one holder is arranged to fix an electronic sub-assembly with respect to the components of the monitor.

6. The device according to claim 4, wherein the at least one holder is made from metal.

7. The device according to claim 6, wherein the at least one screw connects the at least one component of the monitor to the support element in plastic material of the support element.

8. The device according to claim 6, wherein the at least one screw connects the at least one holder to at least a part of the at least one of the plurality of positioning elements of the sheet-metal case, wherein the at least one of the plurality of positioning elements are metal.

9. The device according to claim 1, wherein the support element further comprises a first retaining means located along a periphery of the support element, wherein the first retaining means is configured to secure the support element to a rear case wall of the sheet-metal case, and wherein the first retaining means projects from the side of the support element facing away from the positioning elements of the sheet-metal case.

10. The device according to claim 1, wherein the recess of the support element has a smaller periphery than a recess of the sheet-metal case such that on a front end of the sheet-metal case a predetermined section of the support element is visible while framing the recess of the sheet-metal case on the inside.

11. The device according to claim 1, wherein the components of the monitor comprise at least one touch-sensitive transparent and flat element and an imaging element which are arranged to be stacked in the frame section of the support element and form a touch-sensitive screen.

12. The device according to claim 1, further comprising a sealing element in the form of a flat panel, the sealing element positioned between the support element and the components of the monitor and arranged to provide at least one of a sealing effect or to compensate for tolerances of the components of the monitor.

13. A dialysis machine, comprising the device according to claim 1, wherein the sheet-metal case is a case or body of the dialysis machine.

* * * * *